(12) United States Patent
Jackson

(10) Patent No.: US 10,391,079 B2
(45) Date of Patent: Aug. 27, 2019

(54) METHODS OF DIAGNOSING AND TREATING ALZHEIMER'S DISEASE WITH S-EQUOL

(71) Applicant: Ausio Pharmaceuticals, LLC, Cincinnati, OH (US)

(72) Inventor: Richard L. Jackson, Cincinnati, OH (US)

(73) Assignee: AUSIO PHARMACEUTICALS, LLC, Cincinnati, OH (US)

( * ) Notice: Subject to any disclaimer, the term of this patent is extended or adjusted under 35 U.S.C. 154(b) by 0 days.

(21) Appl. No.: 15/659,114

(22) Filed: Jul. 25, 2017

(65) Prior Publication Data

US 2018/0028491 A1 Feb. 1, 2018

Related U.S. Application Data

(60) Provisional application No. 62/367,002, filed on Jul. 26, 2016.

(51) Int. Cl.
| | | |
|---|---|---|
| *A61K 31/353* | (2006.01) | |
| *C12Q 1/26* | (2006.01) | |
| *C12Q 1/48* | (2006.01) | |
| *C12Q 1/6883* | (2018.01) | |

(52) U.S. Cl.
CPC .............. *A61K 31/353* (2013.01); *C12Q 1/26* (2013.01); *C12Q 1/48* (2013.01); *C12Q 1/6883* (2013.01); *C12Y 109/03001* (2013.01); *C12Y 203/03001* (2013.01); *C12Q 2600/118* (2013.01); *G01N 2800/2821* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 7,396,855 | B2 | 7/2008 | Setchell et al. |
| 7,528,267 | B2 | 5/2009 | Setchell et al. |
| 7,960,432 | B2 | 6/2011 | Setchell et al. |
| 7,960,573 | B2 | 6/2011 | Setchell et al. |
| 8,048,913 | B2 | 11/2011 | Setchell et al. |
| 8,153,684 | B2 | 4/2012 | Lephart et al. |
| 8,263,790 | B2 | 9/2012 | Setchell et al. |
| 8,450,364 | B2 | 5/2013 | Lephart et al. |
| 8,552,057 | B2 | 10/2013 | Brinton et al. |
| 8,580,846 | B2 | 11/2013 | Lephart et al. |
| 8,668,914 | B2 | 3/2014 | Lephart et al. |
| 8,716,497 | B2 | 5/2014 | Setchell et al. |
| 9,408,824 | B2 | 8/2016 | Setchell et al. |
| 9,914,718 | B2 * | 3/2018 | Jackson |
| 2006/0122262 | A1 * | 6/2006 | Lephart |
| 2013/0263298 | A1 | 10/2013 | Michaels et al. |
| 2016/0102070 | A1 | 4/2016 | Jackson |

FOREIGN PATENT DOCUMENTS

| | | |
|---|---|---|
| WO | 2006020269 A2 | 2/2006 |
| WO | 2008016768 A1 | 2/2008 |
| WO | 2008020853 A1 | 2/2008 |
| WO | 2008117027 A2 | 10/2008 |

OTHER PUBLICATIONS

Alzheimer's Association, "What Do We Know About Preventing Alzheimer's Disease?" 2016, 5 pages, downloaded on May 8, 2018 from "https://www.alz.org/national/documents/brochure_prevention.pdf".*
Alzheimer's Association, "Mild Cognitive Impairment (MCI)", 2018, 5 pages, downloaded on Dec. 5, 2018 from "https://www.alz.org/alzheimers-dementia/what-is-dementia/related_conditions/mild-cognitive-impairment".*
Alaynick, William A., "Nuclear Receptors, Mitochondria and Lipid Metabolism," Mitochondrion, 8(4): 329-337 (Sep. 2008).
Bates et al., "Inhibition of N-acetylaspartate production: implications for 1H MRS studies in vivo," Neuroreport, 7 (1996) 1397-1400.
Beattie, Diana S. et al., "The Turnover of the Protein Components of Mitochondria from Rat Liver, Kidney, and Brain," J Biol Chem, vol. 242 No. 20, pp. 4584-4586 (1967).
J.B. Clark, "N-Acetyl Aspartate: A Marker for Neuronal Loss or Mitochondrial Dysfunction," Dev Neurosci, 20 (1998) 271-276.
Fukuyama, Hidenao et al., "Altered Cerebral Energy Metabolism in Alzheimer's Disease: A PET Study," J Nucl Med, vol. 35, No. 1, pp. 1-6 (Jan. 1994).
Gross, Nicholas J. et al., "Apparent Turnover of Mitochondrial Deoxyribonucleic Acid and Mitochondrial Phospholipids in the Tissues of the Rat," J Biol Chem, vol. 244, No. 6, pp. 1552-1562 (1969).
Henigsberg, Neven et al., "1-H MRS Changes in Dorsolateral Prefrontal Cortex after Donepezil Treatment in Patients with Mild to Moderate Alzheimer's Disease," Coll Antropol, 35 Suppl 1: 159-162 (2011).
Hirai, Keisuke et al., "Mitochondrial Abnormalities in Alzheimer's Disease," J Neurosci, 21(9): 3017-3023 (May 1, 2001).
Hjort, Peter F. et al., "Platelet Life Span in Normal, Splenectomized and Hypersplenic Rats," Blood, 15: 45-51 (1960).

(Continued)

*Primary Examiner* — Savitha M Rao
*Assistant Examiner* — Gregg Polansky
(74) *Attorney, Agent, or Firm* — Rothwell, Figg, Ernst & Manbeck, p.c.

(57) ABSTRACT

The present invention provides a method for diagnosing or determining the risk of developing Alzheimer's disease and for treating Alzheimer's disease with S-equol. An aspect of the present invention includes the use of a direct mitochondrial target engagement biomarker to diagnose or assess the risk of developing Alzheimer's disease. Another aspect of the present invention includes the use of a pharmaceutically effective amount of S-equol to treat or prevent Alzheimer's disease in a subject diagnosed with or determined to be at risk of developing Alzheimer's disease.

16 Claims, 3 Drawing Sheets

(56) References Cited

OTHER PUBLICATIONS

Jackson et al., "Emerging evidence of the health benefits of S-equol, an estrogen receptor beta agonist," Nutr Rev, 69 (2011) 432-448.
Jackson et al., "Single-dose and steady-state pharmacokinetic studies of S-equol, a potent nonhormonal, estrogen receptor beta-agonist being developed for the treatment of menopausal symptoms," Menopause (New York, N.Y.), vol. 18, No. 2 (2010) 185-193.
Jenks et al., "A Pilot Study on the Effects of S-Equol Compared to Soy Isoflavones on Menopausal Hot Flash Frequency and Other Menopausal Symptoms," Journal of Women's Health, 21 (2012) 674-682.
Keller et al., "Long-term Effects of Galantamine Treatment on Brain Functional Activities as Measured by PET in Alzheimer's Disease Patients," Journal of Alzheimer's Disease : JAD, 24 (2011) 109-123.
Kennedy et al., "Post Hoc Analyses of ApoE Genotype-Defined Subgroups in Clinical Trials," Journal of Alzheimer's disease : JAD, 50 (2016) 1205-1215.
Khan et al., "Studies of Turnover in Mammalian Subcellular Particles: Brain Nuclei, Mitochondria and Microsomes," J Neurochem, 12 (1965) 81-86.
Klinge, Carolyn M., "Estrogenic Control of Mitochondrial Function and Biogenesis," J Cell Biochem, 105(6): 1342-1351 (Dec. 15, 2008).
Macchi, Zachary et al., "A multi-center screening trial of rasagiline in patients with amyotrophic lateral sclerosis: Possible mitochondrial biomarker target engagement," Amyotrophic Lateral Sclerosis & Frontotemporal Degeneration, 16 (0): 345-352 (Sep. 2015).
McKhann, Guy M. et al., "The diagnosis of dementia due to Alzheimer's disease: Recommendations from the National Institute on Aging—Alzheimer's Association workgroups on diagnostic guidelines for Alzheimer's disease," Alzheimers Dement, 7(3): 263-269 (May 2011).
Menzies, Robert A. and Gold, Philip H., "The Turnover of Mitochondria in a Variety of Tissues of Young Adult and Aged Rats," J Biol Chem, vol. 246, No. 8, pp. 2425-2429 (1971).
Mosconi, Lisa et al., "Reduced Mitochondria Cytochrome Oxidase Activity in Adult Children of Mothers with Alzheimer's Disease," Journal of Alzheimer's Disease : JAD, 27(3): 483-490 (2011).
Nasreddine et al., "The Montreal Cognitive Assessment, MoCA: A Brief Screening Tool for Mild Cognitive Impairment," Journal of the American Geriatrics Society, 53 (2005) 695-699.
Onyango, Isaac G. et al., "Regulation of neuron mitochondrial biogenesis and relevance to brain health," Biochimica et Biophysica Acta, 1802, pp. 228-234 (2010).
Parker et al., "Cytochrome oxidase deficiency in Alzheimer's disease," Neurology, 40 (1990) 1302-1303.
Sanganahalli, Basavaraju G. et al., "Mitochondrial Functional State Impacts Spontaneous Neocortical Activity and Resting State fMRI," PlOS ONE, 8, e63317, 13 pages (May 1, 2013).
Setchell, Kenneth DR et al., "S-Equol, a potent ligand for estrogen receptor β, is the exclusive enantiomeric form of the soy isoflavone metabolite produced by human intestinal bacterial flora," American Journal of Clinical Nutrition, 81:1072-1079 (2005).
Silverman, Daniel H. S. et al., "Positron Emission Tomography in Evaluation of Dementia: Regional Brain Metabolism and Long-Term Outcome," JAMA, vol. 286, No. 17, pp. 2120-2127 (Nov. 7, 2001).
Swerdlow, Russell H., "Bioenergetic medicine," Br J Pharmacol, 171, pp. 1854-1869 (2014).
Swerdlow, Russell H., "Mitochondria and Cell Bioenergetics: Increasingly Recognized Components and a Possible Etiologic Cause of Alzheimer's Disease," Antioxid Redox Signal, vol. 16, No. 12, pp. 1434-1455 (Nov. 12, 2012).
Swerdlow et al., "Mitochondria in Alzheimer's disease," Int Rev Neurobiol, 53 (2002) 341-385.
Usui et al., "Effects of natural S-equol supplements on overweight or obesity and metabolic syndrome in the Japanese, based on sex and equol status," Clinical Endocrinology, 78 (2013) 365-372.
Yao, Jia et al., "Potentiation of Brain Mitochondrial Function by S-equol and R/S-equol Estrogen Receptor β Selective PhytoSERM Treatments," Brain research, 1514: 128-141 (Jun. 13, 2013).
Zhao, Liquin et al., "A Select Combination of Clinically Relevant Phytoestrogens Enhances Estrogen Receptor β-Binding Selectivity and Neuroprotective Activities in Vitro and in Vivo," Endocrinology, 150(2):770-783 (Feb. 2009).
Gustaw-Rothenberg, K. et al., "Biomarkers in Alzheimer's disease: past, present and future," Biomark Med., Feb. 2010, 4(1):15-26.
Neese, S. L. et al., "The effects of dietary treatment with S-equol on learning and memory processes in middle-aged ovariectomized rats," Neurotoxicology and Teratology, 2014, 41:80-88.
Wilkins, H. M., et al., "A Mitochondrial biomarker-based study of S-equol in Alzheimer's Disease subjects: results of a single-arm, pilot trial," Journal of Alzheimer's Disease, 2017, 59:291-300.
Wilkins, H. M., et al., "Platelet cytochrome oxidase and citrate synthase activities in APOE ε4 carrier and non-carrier Alzheimer's disease patients," Redox Biology, 2017, 12:828-832.
Wilkins, H. M., et al., "Trial of S-equol in Alzheimer's Disease (SEAD)," Poster Presentations, Alzheimer's & Dementia: The Journal of the Alzheimer's Association, Jul. 2016, 12(7):P827.
International Search Report and Written Opinion, PCT/US2017/043695, dated Feb. 16, 2018, 28 pages.
Bosetti, F., et al., "Cytochrome c oxidase and mitochondrial F1F0-ATPase (ATP synthase) activities in platelets and brain from patients with Alzheimer's disease," Neurobiology of Aging 23 (2002) 371-376.
Butterfield, D. A. and Halliwell, B., "Oxidative stress, dysfunctional glucose metabolism and Alzheimer disease," Nature 20 (Mar. 2019) 148-160.
Golde, T. E., et al., "Alzheimer's disease: The right drug, the right time," Science 362(6420) (Dec. 14, 2018) 1250-1251.
Mosconi, L., et al., "Perimenopause and emergence of an Alzheimer's bioenergetic phenotype in brain and periphery," PLOS One (Oct. 10, 2017) 1-16.
Parker, W. D., et al., "Reduced platelet cytochrome c oxidase activity in Alzheimer's disease," Neurology 44 (Jun. 1994) 1086-1090.
Valla, J., et al., "Energy hypometabolism in posterior cingulate cortex of Alzheimer's patients: Superficial laminar cytochrome oxidase associated with disease duration," The Journal of Neuroscience 21(13) (Jul. 1, 2001) 4923-4930.

\* cited by examiner

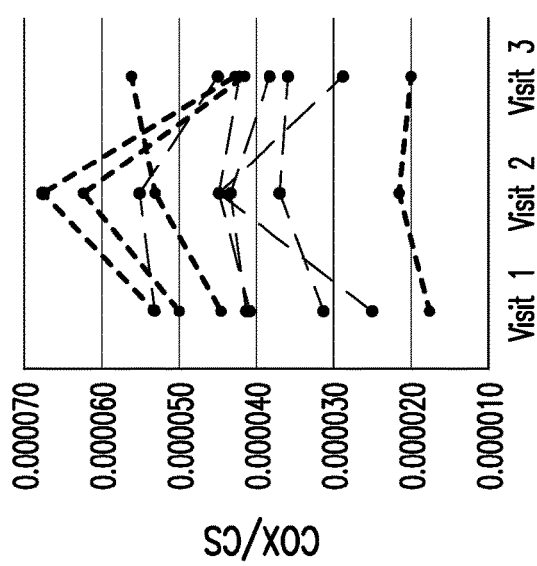
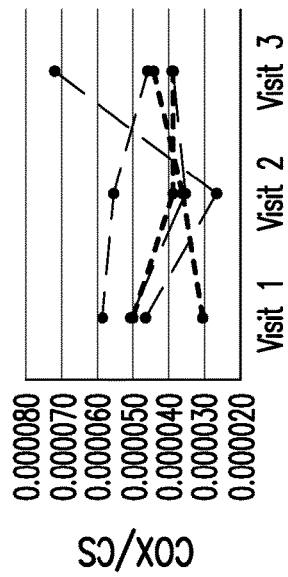
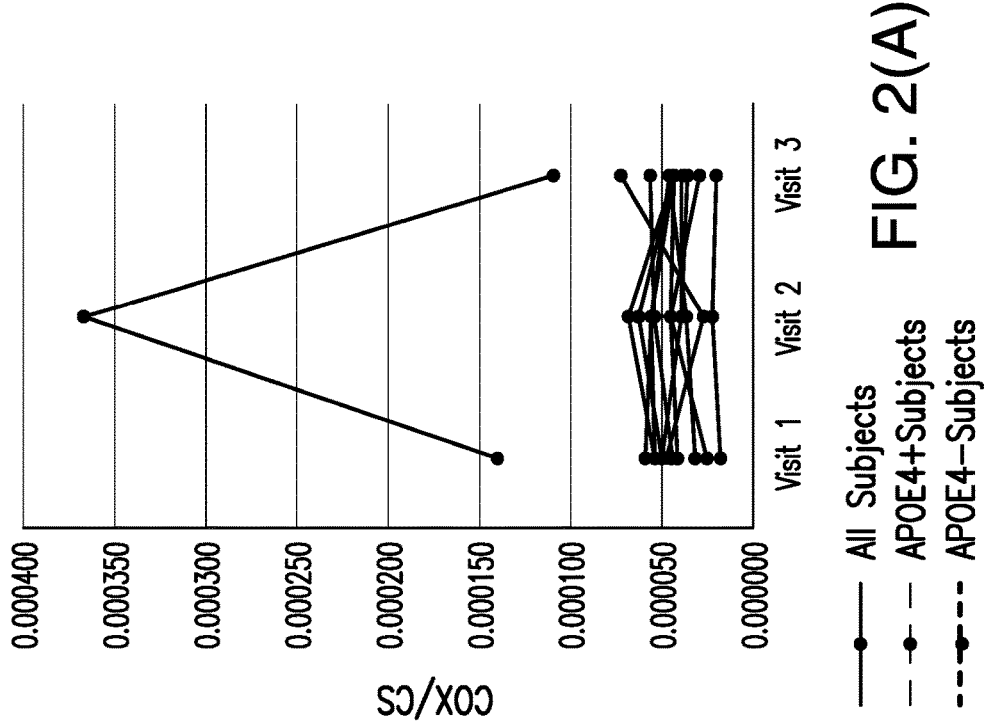
FIG. 2(A)
FIG. 2(B)
FIG. 2(C)

METHODS OF DIAGNOSING AND TREATING ALZHEIMER'S DISEASE WITH S-EQUOL

CROSS-REFERENCE TO RELATED APPLICATIONS

The present application claims the benefit of priority to U.S. Provisional Application Ser. No. 62/367,002, filed on Jul. 26, 2016, which is incorporated herein by reference in its entirety.

BACKGROUND OF THE INVENTION

Field of the Invention

This invention relates to methods of diagnosing and/or treating or preventing Alzheimer's disease with a pharmaceutically effective amount of S-equol or a pharmaceutical composition comprising S-equol. This invention relates to a method of diagnosing and/or treating or preventing Alzheimer's disease using a direct mitochondrial target engagement biomarker platelet cytochrome C oxidase for Alzheimer's disease.

Description of the Related Art

Interventions to eliminate or slow Alzheimer's disease-related cognitive decline and neurodegeneration are urgently needed. Attempts to develop effective interventions currently focus on preventing, reducing, or reversing recognized Alzheimer's disease pathologies, for example by limiting the production or accumulation of brain beta-amyloid peptide Aβ. This approach is too late. The earliest changes in brain function relate to a decrease in brain mitochondria function. In Alzheimer's disease, various mitochondria-localized enzymes show reduced activity with aging. And, in most neurons intact mitochondria are numerically reduced. Perturbed brain glucose and oxygen utilization, changes that could also potentially reflect impaired mitochondrial function, are also observed.

Early-onset, familial Alzheimer's disease, which typically develops before the age of 50, accounts for only a small portion (<5%) of cases. The majority of cases are commonly referred to as late-onset Alzheimer's disease. The elderly constitute a rapidly growing demographic: 10,000 adults turn 65 years of age each day in the United States. An increasing prevalence of neurodegenerative diseases is arguably the biggest downside to this ageing population. For several common neurodegenerative diseases incidence rises with advancing age and prevalence is quite high. Alzheimer's disease, the most common neurodegenerative disease, affects 5.4 million Americans and one in every eight Americans over 65 is estimated to have it. Society is also affected, as families and friends of Alzheimer's disease patients provide most day-to-day care and altogether Alzheimer's disease now costs our economy $385 billion annually.

Alzheimer's disease is polygenic associated with both early- and late-life processes. The human apolipoprotein (APOE) gene exits as four polymorphic alleles: ε1, ε2, ε3, and ε4. Genetically, the ε4 allele of the APOE gene is a risk factor for developing late-onset Alzheimer's disease. It has been reported that carriers of the ε4 allele (APOE4) represent only about 14% of the worldwide population. However, about 40% of the patient population for Alzheimer's disease are APOE4 carriers. The significant increase in the number of APOE4 carriers in patients with Alzheimer's disease as compared to the general population is one reason why research has targeted the APOE4 genotype for late-stage disease.

Associations between aging, Alzheimer's disease, and mitochondrial function are well-documented. Deficits that arise with advancing age tend to exaggerate in Alzheimer's disease. In Alzheimer's disease brains various mitochondria-localized enzymes show reduced activity, and in most neurons intact mitochondria are numerically reduced. Investigators increasingly agree Alzheimer's disease mitochondrial dysfunction is disease-relevant and a reasonable therapeutic target for early stages of the disease.

It has been recently reported that lymphocyte mitochondria membrane potential values served as a biomarker of mitochondrial target engagement in amyotrophic lateral sclerosis patients treated with rasagiline. Macchi et al., *Amyotrophic lateral sclerosis & frontotemporal degeneration*, 16 (2015) 345-352. However, the use of a respiratory chain enzyme as a target engagement biomarker in a therapeutic treatment of Alzheimer's disease has never been reported.

A consistently demonstrated Alzheimer's disease mitochondrial lesion includes reduced cytochrome oxidase (COX) activity. Interestingly, COX activity is reduced in both brain and platelet mitochondria obtained from Alzheimer's disease subjects. While it is only possible to harvest brain mitochondria from autopsy brains, platelets are easily obtained from living subjects and can be serially acquired. For drugs that may enhance mitochondrial function, platelet COX activity offers a unique opportunity for assessing mitochondrial target engagement.

"Mitochondrial medicine" refers to treating disease by therapeutically targeting mitochondria. More recently, the term "bioenergetic medicine" was introduced to describe interventions that specifically increase cell energy production. For a neurodegenerative disease such as Alzheimer's disease, the ideal agent must be systemically safe, cross the blood brain barrier, access neurons, potentially activate mitochondrial biogenesis, and possibly increase mitochondrial respiration.

Estrogen has pro-mitochondrial effects, and estrogen receptor (ER)β may mediate some of those effects. ERβ is found within mitochondria, and ERβ activation reportedly stimulates mitochondrial function. ERβ has also been implicated in mitochondrial biogenesis, the process through which new mitochondria are generated within cells, and which partly determines a cell's mitochondrial mass.

S-equol, an ERβ agonist, was previously shown to increase respiratory and maximal glycolysis fluxes in rat hippocampal neurons, as well as cytochrome oxidase (COX) activity and COX1 protein levels in brains from ovariectomized mice, and S-equol has been studied in human subjects to assess its health impact and safety. Jackson et al., *Nutr Rev,* 69 (2011) 432-448; Yao et al., *Brain research,* 1514 (2013) 128-141; Jenks et al., *Journal of women's health* (2002), 21 (2012) 674-682; Jackson et al. *Menopause* (New York, N.Y.), 18 (2011) 185-193; Usui et al., *Clinical endocrinology,* 78 (2013) 365-372.

S-equol can be produced either chemically (i.e., chemical synthesis) or by biotransformation (biosynthesis) through the metabolism of daidzein, an isoflavone found in soy and red clover, by gut bacteria. The structure of S-equol is shown below.

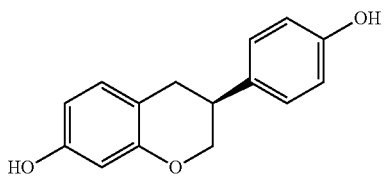 [SMILES: Oc1ccc([C@H]2COc3cc(O)ccc3C2)cc1]

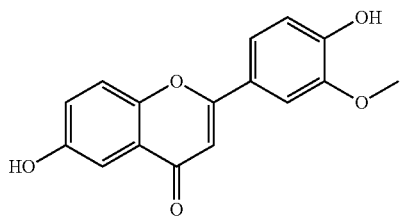

IBSO03569

Equol has a chiral center and therefore can exist in two enantiomeric forms. S-equol, R-equol, racemic equol, and non-racemic mixtures of equol (collectively "equol"); compositions of equol; anhydrous crystalline polymorph of equol; processes for the preparation of equol; and methods of using equol are described in U.S. Pat. No. 8,716,497 (filed Sep. 10, 2012); U.S. Pat. No. 8,048,913 (filed Sep. 14, 2009); U.S. Pat. No. 7,960,432 (filed Jul. 3, 2008); U.S. Pat. No. 7,396,855 (filed Jul. 24, 2003); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005); U.S. Pat. No. 8,668,914 (filed Jul. 31, 2009); U.S. Pat. No. 8,580,846 (filed Aug. 18, 2006); U.S. Pat. No. 8,450,364 (filed Apr. 9, 2012); and U.S. Pat. No. 8,153,684 (filed Oct. 2, 2009); U.S. Pat. No. 9,408,824 (filed Mar. 5, 2014); U.S. Patent Application Publication No. 2016/0102070 (application Ser. No. 14/883,617, filed Oct. 14, 2015); each of which is incorporated by reference in its entirety.

The composition can typically be made by isolating the S-equol enantiomer from a racemic mixture of R-equol and S-equol (also referred to as (.+−.)equol). Typically, the racemic mixture is a synthetic racemic mixture made by a synthetic route, such as the one described herein. Typically, the S-equol composition has an enantiomeric purity of 90% minimum enantiomeric excess ("EE") of S-equol. Typically, more purified compositions can be prepared having an EE of 96% minimum, and even more typically 98% minimum, of S-equol.

The composition of the invention can also comprise a non-racemic mixture of S-equol and R-equol, having an EE for S-equol of more than 0% and less than 90%. A composition that has an EE of 0% is a 50:50 racemic mixture of the two enantiomers. The composition can be made directly from a racemic mixture, by an incomplete separation and removal of R-equol enantiomer from the racemic mixture. The composition can also be made by combining a first equol component comprising a mixture of equol enantiomers, including both a non-racemic mixture and a racemic mixture of equol, with a second component comprising a composition consisting essentially of S-equol. This produces a non-racemic composition that has an excess of S-equol. Conversely, a non-racemic mixture can be prepared with an excess of R-equol enantiomer, by combining a first equol component comprising a mixture of equol enantiomers, including both a non-racemic mixture and a racemic mixture of equol, with a second component comprising a composition consisting essentially of R-equol. Depending upon the specific benefit or indication for the R-equol component and the S-equol component in a composition, a composition can be prepared comprising S-equol and R-equol at a ratio of S-equol to R-equol from greater than about 50:50 to about 99.5:1, more typically about 51:49 to about 99:1, and from less than about 50:50 to about 1:99.5, more typically about 49:51 to about 1:99.

Formulations comprising a mixture of equol, genistein, and daidzein, or a mixture of equol, genistein, daidzein, and IBSO03569 have shown potential for treating or preventing neurodegeneration and Alzheimer's disease. See Zhao et al., *Neuroendocrinology* (2009), 150(2), 770-783; U.S. Pat. No. 8,552,057; Yao et al., *Brain Research*, (2013), 128-141 (collectively "Brinton et al."). Brinton et al., however, does not disclose a direct mitochondrial target engagement biomarker for Alzheimer's disease. And Brinton et al. suggests that such formulation mixtures provide a viable strategy for reducing a risk of Alzheimer's disease in APOE4 carriers. Accordingly, there remains a need in the art for new methods of diagnosing Alzheimer's disease, methods of treating Alzheimer's disease with alternative formulations, and methods for treating Alzheimer's disease patients who are non-carriers of APOE4.

SUMMARY OF THE INVENTION

The following brief summary is not intended to include all features and aspects of the present invention, nor does it imply that the invention must include all features and aspects discussed in this summary.

The inventor has surprisingly found that S-equol, preferably pure and isolated (that is, preferably in the absence of other compounds such as genistein, daidzein, and IBSO03569), can benefit Alzheimer's disease patients. A pilot-scale clinical study of S-equol in Alzheimer's disease has been conducted, using the mitochondrial target engagement platelet biomarker COX as a measure of the primary outcome. The inventor has found that S-equol may be beneficial to Alzheimer's disease patients who do not carry the APOE4 gene. Further, the inventor has found that the mitochondrial target engagement platelet biomarker COX provides a method for diagnosing or detecting a risk of developing Alzheimer's disease in human patients. The inventor has, for the first time, provided a direct mitochondrial target engagement biomarker that can be utilized in the diagnosis or detection, and treatment of Alzheimer's disease.

One embodiment of the present invention is a method for the treatment and/or prevention of Alzheimer's disease comprising administering a pharmaceutically effective amount of a formulation comprising S-equol to a subject in need thereof.

Another embodiment of the present invention is a method for the treatment and/or prevention of Alzheimer's disease comprising administering a pharmaceutically effective amount of a formulation comprising S-equol to a subject diagnosed with Alzheimer's disease.

Another embodiment of the present invention is a method for the treatment and/or prevention of Alzheimer's disease comprising administering a pharmaceutically effective amount of a formulation comprising S-equol to a subject at risk of developing Alzheimer's disease.

Another embodiment of the present invention is a method of diagnosing or determining the risk of developing Alzheimer's disease in a subject, comprising obtaining a blood sample from a subject; directly measuring the activity of one or more mitochondria target engagement biomarkers in said blood sample; and comparing the activity of the one or more mitochondria target engagement biomarker(s) to a library having activity data of the one or more mitochondria target engagement biomarker(s) from one or more subjects diagnosed with Alzheimer's disease.

Another embodiment of the present invention is a method of diagnosing or determining the risk of developing Alzheimer's disease in a subject, comprising obtaining a blood sample from a subject; directly measuring the activity of one or more respiratory chain enzymes in said blood sample; and comparing the activity of the one or more respiratory chain enzymes to a library having activity data of the one or more respiratory chain enzymes from one or more subjects diagnosed with Alzheimer's disease.

Another embodiment of the present invention is a method of diagnosing or determining the risk of developing Alzheimer's disease in a subject, comprising obtaining a blood sample from a subject; directly measuring the activities of the platelet mitochondria cytochrome oxidase (COX) and the citrate synthase (CS) in said blood sample; and comparing the activity of the platelet mitochondria cytochrome oxidase (COX) and the citrate synthase (CS) to a library having activity data of the platelet mitochondria cytochrome oxidase (COX) and the citrate synthase (CS) from one or more subjects diagnosed with Alzheimer's disease.

Another embodiment of the present invention is a method of diagnosing or determining the risk of developing Alzheimer's disease in a subject, comprising obtaining a blood sample from a subject; directly measuring the activity of one or more mitochondria target engagement biomarkers in said blood sample, preferably the activity of one or more respiratory chain enzymes in said blood sample from a subject, more preferably the activities of the platelet mitochondria cytochrome oxidase (COX) and the citrate synthase (CS) in said blood sample from a subject; comparing the measured activity or activities to a library having activity data of the one or more mitochondria target engagement biomarkers, the one or more respiratory chain enzymes, or the platelet mitochondria cytochrome oxidase (COX) and the citrate synthase (CS) from one or more subjects diagnosed with Alzheimer's disease; and repeating the sequence of steps at least one or more times to determine the relative changes in activities for the subject.

Another embodiment of the present invention is a method of diagnosing or determining the risk of developing Alzheimer's disease in a subject and treating a subject in need thereof.

Another embodiment of the present invention is a method of diagnosing or determining the risk of developing Alzheimer's disease in a subject and treating a subject in need thereof, further comprising the step of administering a formulation comprising a pharmaceutically effective amount of S-equol to said subject.

Another embodiment of the present invention is a method of diagnosing or determining the risk of developing Alzheimer's disease; further comprising the step of determining the genotype of said subject.

Another embodiment of the present invention is a method of diagnosing or determining the risk of developing Alzheimer's disease; further comprising the step of determining whether said subject is an apolipoprotein E4 (APOE4) carrier.

Another embodiment of the present invention is a method of diagnosing or determining the risk of developing Alzheimer's disease; further comprising the step of determining whether said subject is an apolipoprotein E4 (APOE4) carrier, and if the subject is not an apolipoprotein (APOE4) carrier, then the step of administering a pharmaceutically effective amount of S-equol to said subject.

Another embodiment of the present invention is a method for alleviating or preventing cognitive decline associated with menopause in a subject, comprising administering to the subject an effective amount of a formulation comprising an amount of S-equol sufficient to alleviate or prevent said cognitive decline.

In another embodiment of the present invention, the subject is a human.

In another embodiment of the present invention, the subject is a human above the age of 50 years.

In another embodiment of the present invention, the S-equol is produced chemically. According to this aspect of the invention, the S-equol is not produced by biotransformation (i.e., biosynthetically). According to this aspect of the invention, the S-equol is not produced from daidzein using a microorganism.

In another embodiment of the present invention, the formulation comprising S-equol is essentially free of genistein, daidzein, and/or IBSO03569.

In another embodiment of the present invention, genistein, daidzein, and/or IBSO03569 are not co-administered with the S-equol.

In another embodiment of the present invention, the S-equol is a single anhydrous crystalline polymorph having characteristic infrared pattern wavenumbers ($cm^{-1}$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461.

In another embodiment of the present invention, the formulation comprising S-equol is essentially free of R-equol.

In another embodiment of the present invention, R-equol is not co-administered with the S-equol.

The foregoing and other objects, features and advantages of the invention will be apparent from the following more particular description of preferred embodiments of the invention, as illustrated in the accompanying drawings in which like reference characters refer to the same parts throughout the different views.

BRIEF DESCRIPTION OF THE DRAWINGS

FIGS. 2(A)-2(C) are graphs showing cytochrome oxidase (COX) and citrate synthase (CS) activity response patterns. FIG. 2(A) is a graph showing response patterns for all 15 participants who completed the study. FIG. 2(B) is a graph showing response patterns for the nine responders with the data from the outlier responder omitted. FIG. 2(C) is a graph showing response patterns for the 5 non-responders.

FIG. 3(A) is a graph showing data from all 7 non-APOE carriers. FIG. 3(B) is a graph showing data from the single non-APOE carrier outlier.

DETAILED DESCRIPTION OF THE INVENTION

Figure 1:
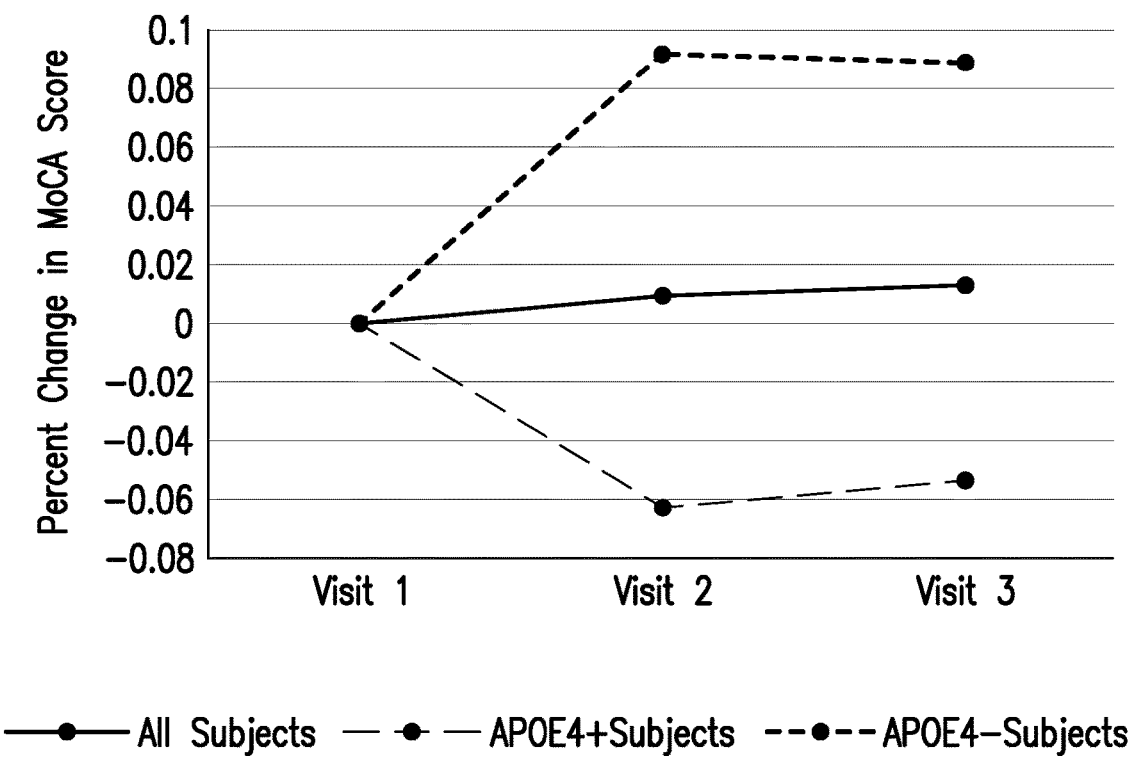
FIG. 1 is a graph showing the inter-visit mean percent change in Montreal Cognitive Assessment (MoCA) scores.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

The term "mitochondrial target engagement biomarker" is meant to define an activity that corresponds to a change in clinical outcome, i.e., an increase in COX activity would result in an improvement of cognitive measurements in a patient with Alzheimer's disease.

The inventor has, for the first time, featured a direct mitochondrial target engagement biomarker in an Alzheimer's disease therapeutic study. Although Fluoro-deoxyglucose positron emission tomography (FDG PET) has been previously used as a biomarker endpoint in other Alzheimer's disease therapeutic studies, FDG PET measures brain glucose utilization and provides only an indirect assessment of mitochondrial function. Similarly, magnetic resonance spectroscopy (MRS) has been used to provide biomarker endpoints in Alzheimer's disease therapeutic studies, and n-acetyl aspartate levels likely relate to mitochondria, but MRS provides, at best, an indirect insight into mitochondrial function. Functional MRI, which quantifies brain regional deoxyhemoglobin and oxyhemoglobin, may provide an indirect assessment of brain mitochondrial function, but MRI has not been shown to be a reliable technique.

Direct mitochondrial assessments currently require laboratory manipulations of cells or tissues. It is impractical to procure brain samples from living Alzheimer's disease subjects, at least in non-surgical trials. Blood, on the other hand, represents an easily procurable tissue. Blood is an advantageous source of tissue because patients are generally more receptive to phlebotomy than they are to biopsy or lumbar puncture procedures.

The inventor has, for the first time, relied on the activity of a respiratory chain enzyme as a target engagement biomarker in any therapeutic trial. Platelet mitochondria COX activity proved to be a useful endpoint, which is in accord with numerous studies that have measured COX activity in Alzheimer's disease subject platelets and found that, similar to what is observed in brain mitochondria, platelet mitochondria COX Vmax activities are lower than they are in age-matched control subjects. COX activity is typically referenced to either mg protein or to CS activity in the assay sample; both are intended to normalize the COX activity to a specified amount of mitochondria.

Secondary outcome measures included safety, cognition, and the relationship of APOE genotype to the cognitive and COX biomarker data. No treatment-related adverse events (either serious or non-serious) were observed. Accordingly, the administration of S-equol at 10 mg twice per day for two weeks, has proven to be safe in Alzheimer's disease patients.

Other dosage amounts and administration schedules for S-equol are contemplated. For example, S-equol can be used one or more times per day at 1-100 mg per dose. Non-limiting examples include 2 mg, 5 mg, 10 mg, 15 mg, 20 mg, 50 mg, etc. The regimen need not be limited to two weeks. No upper limit, with respect to administration schedule, is required.

The S-equol administered is preferably formulation for oral administration; however, other routes of administration are also contemplated, including rectal, optical, buccal (for example sublingual), parenteral (for example subcutaneous, intramuscular, intradermal and intravenous) and transdermal administration.

Compositions or formulations according to the present invention can comprise one or more pharmaceutically-acceptable or industrial standard fillers. The filler must not be deleterious to a subject treated with the composition. The filler can be solid or a liquid, or both. The filler can be formulated with the active S-equol as a unit-dose, for example a tablet, which can typically contain from about 10% to 80% by weight of S-equol. Compositions can be prepared by any of the well known techniques of pharmacy, for example admixing the components, optionally including excipients, diluents (for example water) and auxiliaries as are well known in the pharmaceutical field.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion. Such compositions can be prepared by any suitable method of pharmacy which includes the step of bringing into association the active S-equol and one or more suitable carriers (which can contain one or more accessory ingredients as noted above). In general the compositions of the invention are prepared by uniformly and intimately admixing the S-equol with a liquid or finely divided solid carrier, or both, and then, if necessary, shaping the resulting mixture. For example, a tablet can be prepared by comprising or moulding a powder or granules containing the extract, optionally with one or more accessory ingredients. Compressed tablets can be prepared by compressing in a suitable machine, the extracts in the form of a powder or granules optionally mixed with a binder, lubricant, inert diluents, and/or surface active/dispersing agent(s). Moulded tablets can be made by moulding, in a suitable machine, the powdered compound moistened with an inert liquid binder.

Suitable fillers, such as sugars, for example lactose, saccharose, mannitol or sorbitol, cellulose preparations and/or calcium phosphates, for example tricalcium phosphate or calcium hydrogen phosphate, and also binders such as starch pastes using, for example, corn, wheat, rice or potato starch, gelatin, tragacanth, methylceullose and/or polyvinylpyrrolidone, and, if desired, disintegrators, such as the above-mentioned starches, also carboxymethyl starch, cross linked polyvinyl pyrrolidone, agar or alginic acid or a salt thereof, such as sodium alginate. Excipients can be flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which can comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments can be added to the tablets or dragee coatings, for example for identification purposes or to indicate different doses of active ingredients.

Other orally administrable pharmaceutical compositions are dry-filled capsules made, for example, of gelatin, and soft, sealed capsules made of gelatin and a plasticiser, such as glycerol or sorbitol. The dry-filled capsules can comprise the extracts in the form of granules, for example in admixture with fillers, such as lactose, binders, such as starches, and/or glicants, such as talc or magnesium stearate, and, where appropriate, stabilizers. In soft capsules, the extract is preferably dissolved or suspended in suitable liquids, such as fatty oils, paraffin oil or liquid polyethylene glycols, to which stabilizers can also be added.

According to one aspect of the invention, the compositions comprising S-equol include those described in U.S. Pat. No. 7,960,432 (filed Jul. 3, 2008); U.S. Pat. No. 7,396,855 (filed Jul. 24, 2003); and U.S. Pat. No. 9,408,824 (filed Mar. 5, 2014)—the disclosures of each are hereby incorporated by reference in their entireties.

According to another aspect of the invention, S-equol can be prepared chemically (i.e., chemical synthesis) according to the processes described in U.S. Pat. No. 8,716,497 (filed Sep. 10, 2012); U.S. Pat. No. 8,263,790 (filed Jun. 1, 2011); U.S. Pat. No. 7,960,573 (filed May 4, 2009); U.S. Pat. No. 7,528,267 (filed Aug. 1, 2005)—the disclosures of each are hereby incorporated by reference in their entireties. For example, S-equol can be enantioselectively prepared using an iridium catalyst with a chiral ligand. The methods of enantioselectively preparing S-equol are incorporated by reference.

According to another aspect of the invention, S-equol can be a single anhydrous crystalline polymorph of S-equol, such as the anhydrous crystalline polymorph of S-equol described in U.S. Patent Application Publication No. 2016/0102070 (application Ser. No. 14/883,617, filed Oct. 14, 2015)—the disclosure of which, including the chemical and physical properties used to characterize the anhydrous crystalline polymorph of S-equol, is incorporated by reference in their entireties. For example, the anhydrous crystalline polymorph of S-equol described in U.S. Patent Application Publication No. 2016/0102070 has the following characteristic infrared pattern wavenumbers ($cm^{-1}$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461. The characterizations of anhydrous crystalline polymorph of S-equol are incorporated by reference.

Regarding cognition, the MoCA is typically used to categorize an individual's status as demented versus not demented. The MoCA provides a qualitative measure of the effect of treatments since statistically significant treatment effects would not necessarily be observed. The slope defined by the MoCA visit 1 and 2 scores, however, projected in the direction of improvement in the APOE4 non-carriers, and in the direction of decline in the APOE4 carriers. Therefore, even if the MoCA is generally qualitative, observations and data can be relied on to provide quantifiable trends and projections.

The following examples are provided to aid the understanding of the present invention, the true scope of which is set forth in the appended claims. It is understood that modifications can be made in the procedures set forth without departing from the spirit of the invention.

EXAMPLES

The processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

General Description of Methods and Materials

Alzheimer's disease subjects were recruited through the University of Kansas Alzheimer's Disease Center (ADC). The ADC maintains a clinical cohort whose routine characterizations include Clinical Dementia Rating (CDR) scale ratings, uniform data set (UDS) cognitive testing, and APOE genotyping. The diagnosis of clinic cohort participants is primarily based on CDR and UDS data, and is determined through a consensus conference that includes subspecialty-trained cognitive neurologists and an expert neuropsychologist. Subjects diagnosed with Alzheimer's disease further meet current criteria for that diagnosis in McKhann et al., Alzheimers Dement, 7 (2011) 263-269.

To qualify for the study, participants had to be female with very mild (CDR 0.5) or mild (CDR 1) Alzheimer's disease. Each participant was required to have a study partner. As part of the informed consent process, the subjects and study partners were told that during different parts of the study the participants would receive either an S-equol capsule or an inert placebo. The placebo could not be distinguished from the S-equol by sight, touch, or taste so although the investigators knew whether participants at any given point were receiving S-equol or placebo, the participants themselves were blind to the actual treatment. The S-equol and placebo capsule were provided by Ausio Pharmaceuticals, LLC (Cincinnati, Ohio).

Subjects received a two week supply of medication, which uniformly consisted of placebo, and were instructed to take the study medication twice a day. At the end of this initial two-week period participants returned to the ADC clinical trials unit for their first study visit (visit 1; lead-in evaluation). Visit 1 procedures included an assessment of study medication compliance, vital signs, a query for perceived side effects, the Montreal Cognitive Assessment (MoCA), and a 40 ml phlebotomy; the blood was used to measure platelet mitochondria cytochrome oxidase (COX) and citrate synthase (CS) activities. At the completion of this visit the next two weeks of study medication was dispensed, which uniformly consisted of 10 mg S-equol capsule.

At the end of this second two-week period participants returned to the ADC clinical trials unit for their second study visit (visit 2; active treatment evaluation). The same procedures were performed during the lead-in evaluation and dispensed the next two weeks of study medication, which at this point uniformly consisted of placebo.

At the end of this final two-week period the participants returned to the ADC clinical trials unit for their third study visit (visit 3; wash-out evaluation). The lead-in and active treatment evaluation procedures were performed again, which completed participation in this single-blind study.

Example 1

Obtaining Blood Samples and Measuring Enzyme Activity

Forty milliliter blood samples were collected in tubes containing acid-citrate-dextrose (ACD) tubes as an anticoagulant, and maintained at room temperature. Within 24 hours of phlebotomy the blood was processed by the ADC Mitochondrial Genomics and Metabolism Core. To initiate the processing procedure, platelets were isolated by centrifugation and enriched mitochondrial fractions prepared using previously described methods. Such procedures involved nitrogen cavitation to rupture platelets followed by centrifugation to collect mitochondria.

The protein concentrations of the enriched mitochondrial fractions were measured using a BCA protein assay kit (BioRad, Hercules, Calif.). COX Vmax activity was determined as a pseudo first order-rate constant (sec-1/mg) by measuring the oxidation of reduced cytochrome c at 550 nm.

In addition to measuring COX activity, each sample's citrate synthase (CS) Vmax activity (nmol/min/mg) was measured. This assay was performed spectrophotometrically by following the formation of 5-thio-2-nitrobenzoate (412 nm) following the addition of 100 μM oxaloacetate at 30° C. In addition to referencing COX activities to total protein, potential inter-sample differences in mitochondrial mass was corrected by referencing the COX activity for each sample to its corresponding CS activity.

Example 2

Outcomes

An S-equol-associated modification of platelet mitochondria COX activity was designated as the primary outcome measure. To determine whether an S-equol-associated change in platelet mitochondrial COX activity occurred for an individual participant, an anticipated pattern of response analysis was used. It was expected that platelet mitochondria COX activity would increase in response to the active treatment.

Participants were identified as responding (i.e., increasing COX activity in response to treatment, classified as "successes" or "responders") if the individual change (slope) from the lead-in measurement to the active treatment measurement was greater than the change (slope) from the active-treatment measurement to the wash-out (visit 3) measurement.

Secondary outcomes included a safety analysis of the S-equol 10 mg twice per day dose and an analysis of MoCA scores. Although APOE genotype did not inform subject selection, a post-hoc, secondary analysis of the cognitive and enzyme activity data was conducted after stratifying participants by APOE status.

Example 3

Montreal Cognitive Assessment (MoCA) of APOE4 Carriers and Non-Carriers

A total of 16 participants were enrolled, of which 15 participants completed the study. Data from the other participant was not included in any analysis. Of the 15 subjects, 8 were APOE4 carriers (7 with an APOE3/4 genotype, 1 with an APOE2/4 genotype), and 7 were non-APOE4 carriers (all 7 had an APOE3/3 genotype).

Age means and MoCA score ranges are shown in Table 1. Ages between APOE4 carriers and non-carriers were not significantly different.

TABLE 1

Participant APOE status, ages, and MoCA ranges.

|  | Number of Participants | Age (Mean ± SEM) | Age (Range) | MoCA Baseline (Range) |
|---|---|---|---|---|
| Total | 15 | 73.5 ± 2.0 | 62-89 | 6-25 |
| APOE4 Carriers | 8 | 70.9 ± 2.2 | 63-82 | 7-25 |
| APOE4 non-Carriers | 7 | 76.4 ± 3.4 | 62-89 | 6-17 |

No adverse events occurred and compliance approached 100%. Mean MoCA scores were similar between visits (Table 2). No significant differences were observed between visits, or between APOE4 carriers and non-carriers.

TABLE 2

MoCA scores.

|  | Number of Participants | MoCA Visit 1 (Mean ± SEM) | MoCA Visit 2 (Mean ± SEM) | MoCA Visit 3 (Mean ± SEM) |
|---|---|---|---|---|
| Total | 15 | 14.3 ± 1.5 | 14.6 ± 6.6 | 14.3 ± 1.6 |
| APOE4 Carriers | 8 | 16.4 ± 2.3 | 15.8 ± 2.5 | 15.9 ± 2.7 |
| APOE4 non-Carriers | 7 | 12.0 ± 1.5 | 13.3 ± 2.1 | 12.4 ± 1.6 |

In addition to summarizing MoCA scores by means and standard errors, the percent change between visit 1 and visit 2 scores, as well as the percent change between visit 1 and visit 3 scores, was calculated for each participant.

FIG. 1 is a graph showing inter-visit mean percent change in MoCA scores. The percent change between the visit 1 and visit 2 scores, as well as the visit 1 and visit 3 scores, is shown. The middle (solid) line includes data from all 15 subjects, the bottom (long dashed) line includes data from the 8 APOE4 carriers, and the top (short dashed) line includes data from the 7 non-APOE carriers. FIG. 1 shows that between visit 1 and visit 2 the percent MoCA score changes trended in a downward direction for APOE4 carriers, and in an upward direction for APOE4 non-carriers.

APOE status did not have an appreciable impact on the primary outcome measure, as defined above. Patients who are APOE4 carriers and non-carriers showed roughly equivalent proportions of responders and non-responders. However, the slope defined by the visit 1 and 2 COX/CS activities trended higher in the APOE4 non-carriers than it did in the APOE4 carriers, and that trends between the visit 2 and 3 measurements could be consistent with a wash-out effect. Thus, observations and data can be relied on to provide quantifiable trends and projections for APOE4 carriers and non-carriers.

Example 4

Cytochrome Oxidase (COX) and Citrate Synthase (CS) Activities of APOE4 Carriers and Non-Carriers After correcting for the degree of mitochondrial enrichment for each assayed sample by referencing COX activity to CS activity, 11 of the 15 participants were found to have a positive response pattern.

FIGS. 2(A)-2(C) show COX/CS response patterns. FIG. 2(A) is a graph showing the response patterns for all 15 participants who completed the study. Data from one participant, a non-APOE4 carrier who showed a positive response pattern, are several-fold higher than that of the other 14 participants. FIG. 2(B) eliminates the outlier responder and includes only data from the other 10 responders, and illustrates the inter-visit changes for the responder participants. FIG. 2(C) is a graph that includes data from the 5 non-responders, and illustrates the inter-visit changes for each non-responder participant. In FIGS. 2(B) and 2(C), the APOE4 carrier participants are shown in a long-dashed line, and non-APOE4 carrier participants are shown in a short-dashed line.

FIG. 2(A) shows the COX/CS response patterns for all 15 participants who completed the study, and is included specifically to illustrate that one of the participants, a non-APOE4 carrier that was counted as a responder, generated COX/CS values that were several-fold higher than the data from the other 14 participants.

FIG. 2(B) shows the COX/CS pattern for each participant that qualified as a responder, with the exception of the outlier non-APOE4 carrier responder. FIG. 2C shows the COX/CS pattern for each participant that qualified as a non-responder. Responder status was not obviously contingent on APOE genotype. Table 3 summarizes the mean COX/CS values, with and without including the data from the outlier participant. No significant differences were observed between visits, or between APOE4 carriers and non-carriers.

TABLE 3

COX/CS values.

| | Number of Participants | COX/CS Visit 1 (Mean ± SEM) | COX/CS Visit 2 (Mean + SEM) | COX/CS Visit 3 (Mean ± SEM) |
|---|---|---|---|---|
| Total | | | | |
| Outlier Included | 15 | 4.9E−05 ± 7.2E−06 | 6.6E−05 ± 2.2E−05 | 4.7E−05 ± 5.4E−06 |
| Outlier Excluded | 14 | 4.3E−05 ± 3.2E−06 | 4.5E−05 ± 3.5E−06 | 4.2E−05 ± 3.2E−06 |
| APOE4 Carriers | 8 | 4.4E−05 ± 4.0E−06 | 4.3E−05 ± 3.5E−06 | 4.4E−05 ± 4.5E−06 |
| APOE4 non-Carriers | | | | |
| Outlier Included | 7 | 5.5E−05 ± 1.5E−05 | 9.2E−05 ± 4.6E−05 | 5.1E−05 ± 1.1E−05 |
| Outlier Excluded | 6 | 4.1E−05 ± 5.7E−06 | 4.7E−05 ± 7.1E−06 | 4.1E−05 ± 4.8E−06 |

Figure 3A:
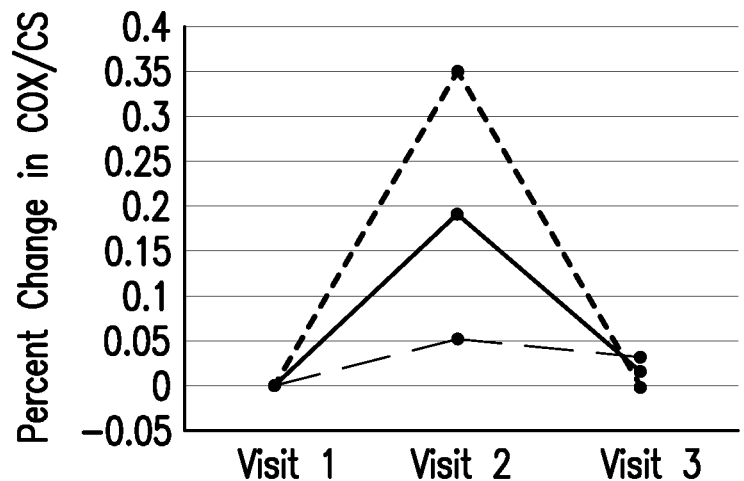
FIGS. 3(A) and 3(B) are graphs of the inter-visit mean percent change in COX/CS values.
Figure 3B:
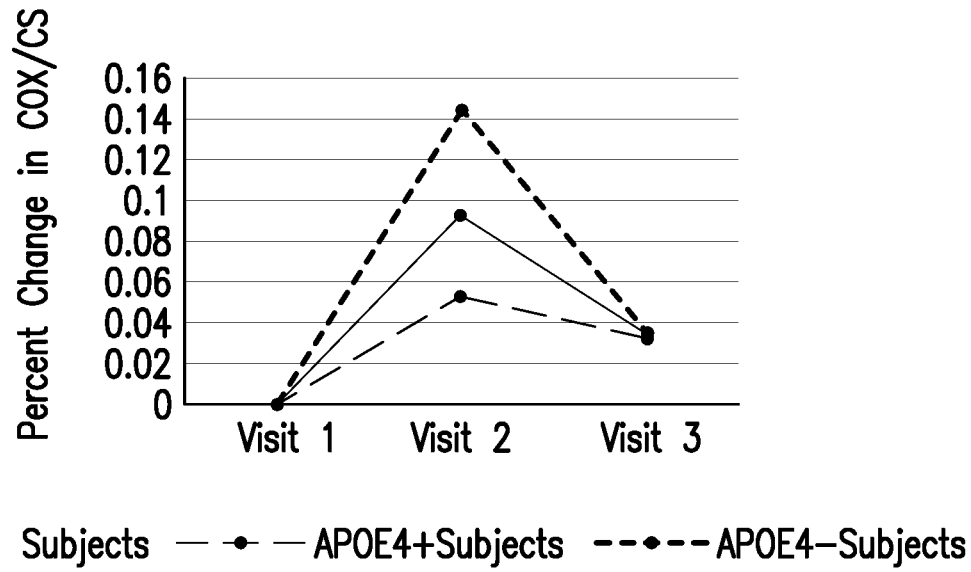

FIGS. 3(A) and 3(B) are graphs showing inter-visit mean percent change in COX/CS values. The percent change between the visit 1 and visit 2 scores, as well as the visit 1 and visit 3 scores, is shown. The solid line includes data from all 15 subjects; the long-dashed line includes data from only the 8 APOE4 carriers. In FIG. 3(A), the short-dashed line includes data from all 7 non-APOE carriers, and in FIG. 3(B) the short-dashed line excludes data from the single non-APOE carrier outlier. While no significant differences between visits were similarly observed with this analysis, between visit 1 and visit 2 the percent COX/CS change trended higher in the non-APOE4 carriers than it did in the APOE4 carriers. Qualitative trends consistent with a possible "wash-out" effect were also apparent.

The examples herein demonstrate the use of a direct mitochondrial target engagement biomarker to inform an Alzheimer's disease treatment trial.

While this invention has been particularly shown and described with references to preferred embodiments thereof, it will be understood by those skilled in the art that various changes in form and details may be made therein without departing from the scope of the invention encompassed by the appended claims.

REFERENCES

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

Setchell et al., S-Equol, a potent ligand for estrogen receptor b, is the exclusive enantiomeric form of the soy isoflavone metabolite produced by human intestininal bacterial flora, American *Journal of Clinical Nutrition*, 2005, 81:1072-1079.

R. H. Swerdlow, Bioenergetic medicine, *Br J Pharmacol*, 171 (2014) 1854-1869.

R. H. Swerdlow, Mitochondria and cell bioenergetics: increasingly recognized components and a possible etiologic cause of Alzheimer's disease, *Antioxid Redox Signal*, 16 (2012) 1434-1455.

Hirai et al., Mitochondrial abnormalities in Alzheimer's disease, *J Neurosci*, 21 (2001) 3017-3023.

Silverman et al., Positron emission tomography in evaluation of dementia: Regional brain metabolism and long-term outcome, *JAMA*, 286 (2001) 2120-2127.

Fukuyama et al., Altered cerebral energy metabolism in Alzheimer's disease: a PET study, *J Nucl Med*, 35 (1994) 1-6.

C. M. Klinge, Estrogenic control of mitochondrial function and biogenesis, *J Cell Biochem*, 105 (2008) 1342-1351.

W. A. Alaynick, Nuclear receptors, mitochondria and lipid metabolism, Mitochondrion, 8 (2008) 329-337.

Onyango et al., Regulation of neuron mitochondrial biogenesis and relevance to brain health, *Biochimica et biophysica acta*, 1802 (2010) 228-234.

Jackson et al., Emerging evidence of the health benefits of S-equol, an estrogen receptor beta agonist, *Nutr Rev*, 69 (2011) 432-448.

Yao et al., Potentiation of brain mitochondrial function by S-equol and R/S-equol estrogen receptor beta-selective phytoSERM treatments, *Brain research*, 1514 (2013) 128-141.

Jenks et al., A pilot study on the effects of S-equol compared to soy isoflavones on menopausal hot flash frequency, *Journal of women's health* (2002), 21 (2012) 674-682.

Jackson et al., Single-dose and steady-state pharmacokinetic studies of S-equol, a potent nonhormonal, estrogen receptor beta-agonist being developed for the treatment of menopausal symptoms, *Menopause* (New York, N.Y.), 18 (2011) 185-193.

Usui et al., Effects of natural S-equol supplements on overweight or obesity and metabolic syndrome in the Japanese, based on sex and equol status, *Clinical endocrinology*, 78 (2013) 365-372.

McKhann et al., The diagnosis of dementia due to Alzheimer's disease: Recommendations from the National Institute on Aging-Alzheimer's Association workgroups on diagnostic guidelines for Alzheimer's disease, *Alzheimers Dement*, 7 (2011) 263-269.

Mosconi et al., Reduced mitochondria cytochrome oxidase activity in adult children of mothers with Alzheimer's disease, *Journal of Alzheimer's disease*: JAD, 27 (2011) 483-490.

Parker et al., Cytochrome oxidase deficiency in Alzheimer's disease, *Neurology*, 40 (1990) 1302-1303.

Keller et al., Long-term effects of galantamine treatment on brain functional activities as measured by PET in Alzheimer's disease patients, *Journal of Alzheimer's disease: JAD*, 24 (2011) 109-123.

Henigsberg et al., 1-H MRS changes in dorsolateral prefrontal cortex after donepezil treatment in patients with mild to moderate Alzheimer's disease, *Coll Antropol*, 35 Suppl 1 (2011) 159-162.

Bates et al., Inhibition of N-acetylaspartate production: implications for 1H MRS studies in vivo, *Neuroreport*, 7 (1996) 1397-1400.

J. B. Clark, N-acetyl aspartate: a marker for neuronal loss or mitochondrial dysfunction, *Dev Neurosci*, 20 (1998) 271-276.

Sanganahalli et al., Mitochondrial functional state impacts spontaneous neocortical activity and resting state FMRI, *PloS one*, 8 (2013) e63317.

Macchi et al., A multi-center screening trial of rasagiline in patients with amyotrophic lateral sclerosis: Possible mitochondrial biomarker target engagement, *Amyotrophic lateral sclerosis & frontotemporal degeneration*, 16 (2015) 345-352.

Swerdlow et al., Mitochondria in Alzheimer's disease, *Int Rev Neurobiol*, 53 (2002) 341-385.

Hjort et al., Platelet life span in normal, splenectomized and hypersplenic rats, *Blood*, 15 (1960) 45-51.

R. A. Menzies, P. H. Gold, The turnover of mitochondria in a variety of tissues of young adult and aged rats, *J Biol Chem*, 246 (1971) 2425-2429.

Beattie et al., The turnover of the protein components of mitochondria from rat liver, kidney, and brain, *J Biol Chem*, 242 (1967) 4584-4586.

Khan et al., Studies of Turnover in Mammalian Subcellular Particles: Brain Nuclei, Mitochondria and Microsomes, *J Neurochem*, 12 (1965) 81-86.

Gross et al., Apparent turnover of mitochondrial deoxyribonucleic acid and mitochondrial phospholipids in the tissues of the rat, *J Biol Chem*, 244 (1969) 1552-1562.

Nasreddine et al., The Montreal Cognitive Assessment, MoCA: a brief screening tool for mild cognitive impairment, *Journal of the American Geriatrics Society*, 53 (2005) 695-699.

Kennedy et al., Post Hoc Analyses of ApoE Genotype-Defined Subgroups in Clinical Trials, *Journal of Alzheimer's disease: JAD*, 50 (2016) 1205-1215.

Yao et al., Potentiation of brain mitochondrial function by S-equol and R/S-equol estrogen receptor β-selective phytoSERM treatments, *Brain Research*, (2013) 128-151.

The invention claimed is:

1. A method for improving a cognitive measurement in a patient at risk of or diagnosed with Alzheimer's disease comprising administering a pharmaceutically effective amount of a formulation comprising S-equol to said patient, wherein there is an absence of genistein, daidzein, and/or IBS003569 in said formulation, and wherein said administration results in an increased ratio of platelet mitochondria cytochrome oxidase (COX) to citrate synthase (CS) in a blood sample obtained from said patient.

2. The method of claim 1, wherein the patient has been diagnosed with Alzheimer's disease.

3. The method of claim 1, wherein the patient is at risk of developing Alzheimer's disease.

4. The method of claim 1, wherein said patient is a human.

5. The method of claim 4, wherein said patient is a human above the age of 50.

6. The method of claim 1, wherein the S-equol is produced chemically.

7. The method of claim 1, wherein the S-equol is not produced biosynthetically or by biotransformation.

8. The method of claim 1, wherein the S-equol is a single anhydrous crystalline polymorph having the following characteristic infrared pattern wavenumbers ($cm^{-1}$): 3433, 3023, 3003, 2908, 2844, 1889, 1614, 1594, 1517, 1508, 1469, 1454, 1438, 1400, 1361, 1323, 1295, 1276, 1261, 1234, 1213, 1176, 1156, 1116, 1064, 1020, 935, 897, 865, 840, 825, 810, 769, 734, 631, 616, 547, 517, 480, and 461.

9. The method of claim 1, wherein genistein, daidzein, and/or IBSO03569 are not co-administered with S-equol.

10. The method of claim 1, wherein the formulation has an enantiomeric purity of 90% minimum enantiomeric excess ("EE") of S-equol.

11. The method of claim 1, wherein the cognitive measurement is assessed using a Montreal Cognitive Assessment (MoCA) test.

12. The method of claim 1, wherein S-equol is administered at 1-100 mg/dose per day.

13. The method of claim 1, wherein S-equol is administered at 10 mg/dose per day.

14. The method of claim 1, wherein S-equol is administered at 50 mg/dose per day.

15. The method of claim 1, wherein S-equol is administered twice daily.

16. The method of claim 1, wherein S-equol is administered for at least two weeks.

* * * * *